United States Patent [19]

Lardy

[11] Patent Number: 5,292,730
[45] Date of Patent: Mar. 8, 1994

[54] MODULATION OF IMMUNE SYSTEM WITH Δ5 -ANDROSTENES

[75] Inventor: Henry A. Lardy, Madison, Wis.

[73] Assignee: Humanetics Corporation, Chaska, Minn.

[21] Appl. No.: 922,850

[22] Filed: Jul. 31, 1992

Related U.S. Application Data

[63] Continuation-in-part of Ser. No. 867,288, Apr. 10, 1992, which is a continuation of Ser. No. 575,156, Aug. 29, 1990, abandoned.

[51] Int. Cl.$^5$ ............................................. A61K 31/56
[52] U.S. Cl. .................... 514/171; 514/169; 514/885
[58] Field of Search ................ 514/171, 127, 169, 120

[56] References Cited

U.S. PATENT DOCUMENTS 5,077,284 12/1981 Loria et al. ..................... 514/171

Primary Examiner—Frederick E. Waddell
Assistant Examiner—T. J. Griares
Attorney, Agent, or Firm—Faegre & Benson

[57] ABSTRACT

Alzheimer's disease and immune deficiency disorders may be effectively treated by administering a Δ5-Androstene-3β-ol-17-one having a $C_7$ substituent selected from the group consisting of oxo, hydroxy and groups convertible thereto by hydrolysis.by administering a therapeutic amount of a Δ5-Androstene-3β-ol-17-one having a $C_7$ substituent selected from the group consisting of oxo, hydroxy and groups convertible thereto by hydrolysis.

4 Claims, No Drawings

MODULATION OF IMMUNE SYSTEM WITH Δ5-ANDROSTENES

This is a continuation-in-part of U.S. patent application Ser. No. 867,288 filed 10 Apr. 1992, pending which is a continuation of U.S. patent application Ser. No. 575,156 filed 29 Aug. 1990, now abandoned.

FIELD OF THE INVENTION

Broadly, the invention relates to the use of steroids for effecting a desired biological response. Specifically, the invention relates to the use of Δ5-androstenes for retarding the degenerative effects of Alzheimer's disease and modulating the antibody responsiveness of the immune system.

BACKGROUND

Alzheimer's Disease

Alzheimer's disease is a degenerative brain disease characterized by the loss of nerve cells in the cerebral cortex. The disease is the leading cause of presenile dementia. Among the deleterious effects are speech disturbances, severe short term memory loss and disorientation. The disease results in a progressive loss of the mental facilities.

Despite years of extensive research, investigators have yet to understand the cause of the disease and have to date been unable to find an effective treatment. However, it is generally thought that the disease is associated with a deficiency of the neurotransmitter acetylcholine.

Accordingly, a substantial need exists for a therapeutic agent effective for retarding the deleterious effects of Alzheimer's disease.

Immune Response

The immune system protects against the introduction and advancement of pathogenic microorganisms through activation of T and B lymphocytes abd macrophages. Upon detection of an antigen, such as a pathogenic microorganism, T cells are activated to produce lymphokines that influence the activities of other host cells and the B cells mature to produce immunoglobulins or antibodies that react with the antigen.

Immune senescence results in a decrease in the antibody responsiveness of the immune system and thereby retards the ability of the system to immunize the body against pathogenic microorganisms. Such a depressed immune system results in an increase in the frequency and severity of pathogenically induced maladies and possibly death.

Immune senescence may result as a natural consequence of aging or as a deleterious effect of pathological microorganism(s). Immune senescence is one of the major health problems of our time with a general consensus and within the medical profession that the problem may soon reach epidemic proportions.

Accordingly, a substantial need exists for a therapeutic agent effective for inducing an immunomodulatory response to immune senescence.

SUMMARY OF THE INVENTION

Alzheimer's Disease

Alzheimer's disease may be treated by administering a therapeutic amount of a Δ5-Androstene-3βol-17one having a $C_7$ substituent selected from the group consisting of oxo, hydroxy and groups convertible thereto by hydrolysis. Such treatment is effective for retarding the degenerative effects of Alzheimer's disease, including specifically, but not exclusively, deterioration of the central nervous system, loss of metal facilities, loss of short term memory, and disorientation.

These steroids are particularly effective for use in treating Alzheimer's disease as they, contrary to other Δ5-Androstenes, provide the desired biological response without stimulating the undesired production of additional sex hormones.

Immune Response

Immune senescence may be modulated by administering a therapeutic amount of a Δ5-Androstene-3β-ol-17-one having a $C_7$ substituent selected from the group consisting of oxo, hydroxy and groups convertible thereto by hydrolysis.

These steroids are particularly effective for modulating the immune system as they, contrary to other Δ5-Androstenes, provide the desired biological response without stimulating the undesired production of additional sex hormones.

DETAILED DESCRIPTION OF THE INVENTION INCLUDING A BEST MODE

Alzheimer's disease and immune deficiency disorders may be effectively treated by administering a Δ5-Androstene-3β-ol-17-one having a $C_7$ substituent selected from the group consisting of oxo, hydroxy and groups convertible thereto by hydrolysis.

These steroids may also be administered as a carbamate, enanthate or other such derivative capable of releasing the specified steroid within the intestinal tract, blood and/or body tissues.

Synthesis (1) Δ5-Androstene 3β,7-diol, 17-one (7-hydroxy DHEA)

Δ5-Androstene 3β,7α-diol, 17-one (7-hydroxy DHEA) can be synthesized from commercially available DHEA acetate (10) by sequentially synthesizing:

Δ5-Androstene-3β hydroxy-17-one acetate
Δ5-Androstene-3β-hydroxy-7-bromo-17one
Δ5-Androstene-3β,7α-hydroxy-17one diacetate
Δ5-Androstene-3β,17α-hydroxy-17-one Δ5-Androstene 3β-hydroxy-7-bromo-17-one (7-bromo DHEA) can be synthesized from Δ5-Androstene 3β-hydroxy-17-one acetate (DHEA acetate) by reacting the DHEA acetate with a brominating agent such as Dibromantin (1,3 dibromo 5,5 dimethylhydantoin or N-bromo succinimide. The 7-bromo DHEA is unstable and must be used immediately in the next step of the process.

The 7-bromo DHEA containing an isomeric mixture of 7α-bromo DHEA and 7β-bromo DHEA may be equilibrated to 7α-bromo DHEA in accordance with the method described for a cholesterol derivative in Confalone, P.N., Kulesha, I.D., and Uskokovic, M.R. Jour. Org. Chem., vol. 46, pp 1030–1032 (198). Briefly the racemic mixture of 7-bromo DHEA is contacted with cold anhydrous LiBr and shielded from light until the stereospecific composition is achieved.

Δ5-androstene 3β, 7-hydroxy-17-one diacetate (7-hydroxy DHEA diacetate) may be synthesized from the 7-bromo DHEA by reacting the 7-bromo DHEA with a mixture of glacial acetic acid and powdered silver acetate at room temperature in a suitable solvent such as methylene chloride or acetone.

Δ5-androstene 3β, 7α-hydroxy-17-one (7-hydroxy DHEA) 2 may be synthesized from the 7-hydroxy DHEA diacetate by reacting the 7-hydroxy DHEA diacetate dissolved in methanol with an aqueous solution containing a suitable base such as $Na_2CO_3$.

The synthesized 7-hydroxy DHEA may then be purified by (i) evaporating the methanol in vacuo, (ii) extracting the 7-hydroxy DHEA into an appropriate organic solvent such as dichloromethane, (iii) evaporating the organic solvent in vacuo, (iv) azeotropically drying the extracted solids containing the 7-hydroxy DHEA with a suitable organic solvent such as ethanol, (v) dissolving the extracted solids in acetone, and then (vi) adding a suitable precipitating agent, such as hexane, to the acetone solution to produce purified crystals of Δ5-Androstene 3β,7α-diol, 17-one (7-hydroxy DHEA).

A second crop of Δ5-Androstene-3β,7α-diol-17-one (7-hydroxy DHEA) crystals may be obtained by cooling the resultant solution below room temperature.

(2) Δ5-Androstene-3βol 7,17-dione (7-keto DHEA)

Δ5-Androstene 3β-ol-7,17-dione can be synthesized from commercially available DHEA acetate by sequentially synthesizing:

3β-acetoxy-Δ5-androstene-17-one
3β-acetoxy-Δ5-androstene-7,17-dione
Δ5-androstene 3β-hydroxy-7,17-dione 3β-acetoxy-Δ5-androstene-7,17-dione (7-oxo DHEA acetate) can be synthesized from 3β-acetoxy-Δ5-androstene-17-one (DHEA acetate) by reacting the DHEA acetate with the oxidizing agent $CrO_3$ in accordance with the procedure outlined in Fieser, L.F., *Jour. Am. Chem. Soc.*, vol. 75, pp 4386–4394 (1953).

Δ5-androstene 3β-hydroxy-7,17-dione (7-one DHEA) can be synthesized from the 7-one DHEA acetate and purified by employing the deesterification and purification steps set forth above with respect to the synthesis and purification of 7-hydroxy DHEA from 7-hydroxy DHEA diacetate.

Treatment

A subject may be treated with the steroids specified herein by any of the commonly accepted practices including ingestion or injection. It is believed that treatment at a dosage rate of about 0.1 to 2 grams of steroid per 100 kilograms of body weight per day, preferably 0.5 to 2 grams of steroid per 100 kilograms of bodyweight per day, is generally effective for triggering the desired biological responses. A dose rate of less than about 0.1 grams per 100 kilograms bodyweight is generally believed to be insufficient to trigger the desired biological response while a dose rate of greater than about 2 grams per 100 kilograms bodyweight is believed to result in an increase in the cost of the treatment without providing a corresponding benefit in performance. The optimum dose rate to be administered to a subject is case specific as the optimum dose rate depends upon several factors including current body composition (percent fat), age, and the like.

Without intending to be limited thereby, we believe that the steroids specified herein are metabolic intermediates along the pathway to conversion of DHEA to an ultimate metabolite(s) which is responsible for treatment of Alzheimer's disease.

A subject may be treated with one of the steroids specified herein on substantially any desired schedule. However, it is believed that the steroids themselves are not stored within the body and are substantially removed and/or deactivated within hours after administration. Accordingly, for optimum effectiveness the subject under treatment should be treated at least about every day. For reasons of convenience the subject under treatment may be treated less frequently, such as every other day or once a week, when less than maximum performance is acceptable.

As is apparent from the factors which affect dosage and dose rate, each particular subject should be carefully and frequently reviewed and the dosage and/or dose rate altered in accordance with the particular situation.

EXPERIMENTAL

EXAMPLE I

Synthesis

Δ5-Androstene 3β, 7α-diol-17-one (7-hydroxy DHEA)

(Step 1) Into a two liter, triple neck, round bottom flask equipped with a magnetic stirrer and a reflux condenser was placed 1000 ml hexane (b.p 69–71°), 10 grams (0.03 moles) DHEA acetate and 13.6 grams (0.16 moles) $NaHCO_3$ to form a first mixture. The first mixture was placed under a $N_2$ atmosphere and heated under constant agitation to reflux. Into the refluxing first mixture was added 6.11 grams (0.02 moles) Dibromantin (1,3 dibromo 5,5 dimethylhydantion) as a brominating agent to form a second solution. The second solution gradually turned orange after which it rapidly turned a pale white/yellow. The second solution was refluxed for 30 minutes, cooled to room temperature and filtered through a sintered glass funnel. The residue was rinsed with 50 ml dichloromethane and the combined filtrate rotovapped to dryness at a temperature of less than 35° C. The dry filtrate (Δ5-Androstene 3β-ol-7-bromo-17-one) is unstable to storage and was used immediately in step two.

(Step 2) The dry filtrate was resolubilized in 80 ml of dichloromethane in a one liter stoppered flask equipped with a magnetic stirrer and placed in an ice bath. Into the resolubilized filtrate was added 8 grams anhydrous LiBr in 320 ml ice-cold acetone to form a third solution. The third solution was shielded from light and stirred continuously for three hours. The resulting solution containing predominantly (Δ5-Androstene 3β-ol-7α-bromo-17-one) was allowed to warm briefly and used immediately in step three.

(Step 3) Into a 500 ml flask equipped with a magnetic stirrer was placed 320 ml dichloromethane, 80 ml glacial acetic acid, and 26 grams of silver acetate to form a first suspension. The first suspension was stirred continuously for 20 minutes at room temperature. The stirred first suspension was added under constant agitation into the solution of predominantly Δ5-Androstene 3β-ol-7α-bromo-17-one to form a second suspension. The second suspension was constantly stirred for 30 minutes at room temperature after which the suspension was filtered through a sintered glass funnel to produce separate a solid fraction. The filtered solid fraction was rinsed with 100 ml dichloromethane. The filtrate was extracted three times with 1000 ml of water, remaining acetic acid was neutralized with 5% $NaHCO_3$ solution, and the dichloromethane solution was extracted twice more with water. The organic solution containing Δ5-

Androstene 3β-17α-diol-17-one diacetate was then rotovapped to dryness.

(Step 4) The dried extracted solids were resolubilized in 500 ml methanol in a one liter, triple necked flask equipped with a magnetic stirrer and a reflux condenser to form a fourth solution. The fourth solution was placed under a N₂ atmosphere and heated under constant stirring to reflux. Into the fourth solution was added 250 ml of a 5% aqueous solution of Na₂CO₃ to form a fifth solution. The fifth solution was refluxed under constant agitation for 45 minutes. The methanol was rotovapped off and the aqueous fifth solution carefully brought to a pH of 7 with an appropriate amount of glacial acetic acid. The neutralized fifth solution was extracted twice with 100 ml of dichloromethane. The dichloromethane solution of Δ5-Androstene 3β, 7αdiol-17-one was rotovapped to near dryness, azeotropically dried with absolute ethanol, and then azeotropically dried twice with acetone. Warm acetone was added to the dried extracted solids until the solids were completely dissolved to form a sixth solution. Hexane was added to the sixth solution until the solution began to cloud at which time crystals of α5-Androstene 3β-7α-diol-17-one began to form at room temperature.

A second crop of α5-Androstene 3β-7α-diol-17-one crystals was obtained by cooling the remaining sixth solution.

The product melts at about 187-189° C. and when recrystallized from acetone/hexane melts at about 192-193° C.

EXAMPLE II

Synthesis

Δ5-Androstene 3β-7(αβ)-diol-17-one 7αβ-hydroxy DHEA

Δ5-Androstene 3β-7α-diol-17-one was manufactured in accordance with the procedure set forth in Example I except that Step 2 was eliminated with the dried filtrate from Step I simply resolubilized in the 80 ml of dichloromethane in preparation for Step 3.

EXAMPLE III

Synthesis

Δ5-Androstene 3β-ol-7,17-dione 7αβ-keto DHEA (Step 1) Into a 50 ml flask equipped with a magnetic stirrer and a water bath was placed 6.5 ml acetic anhydride, 23 ml acetic acid, 17 grams sodium acetate, and 2 grams DHEA acetate to form a first mixture. Into the first mixture was added 2 grams chromium trioxide over a thirty minute period to form a second mixture. The first mixture was maintained at a constant temperature of 56-58° C. and continuously agitated during addition of the chromium trioxide. The second mixture was maintained at 56-58° C. and continuously agitated for an additional hour after which the second mixture was cooled and slowly poured under continuous agitation into 600 ml of ice water to form a precipitate. The flocculent precipitate was collected on a sintered glass funnel and washed with water until no longer green. After drying in vacuo over P₂O₅ the product was dissolved in methanol and recrystallized to yield substantially pure Δ5-Androstene 3β-acetoxy-7,17-dione having a melting point of about 191-192° C.

(Step 2) The precipitate was resolubilized in 500 ml of methanol in a one liter, triple necked, round bottom flask equipped with a magnetic stirrer and reflux condenser to form a third solution. The third solution was placed under a N₂ atmosphere and heated under constant agitation to reflux. Into the third solution was added 250 ml of a 5% solution of Na₂CO₃ to form a fourth solution. The fourth solution was refluxed under constant agitation for 45 minutes. The methanol was rotovapped off and the aqueous fourth solution carefully brought to a pH of 7 with an appropriate amount of glacial acetic acid. The neutralized fourth solution was extracted with two 100 ml portions of dichloromethane, and two portions combined, and the dichloromethane evaporated in vacuo. The extracted solids were then azeotropically dried first with absolute ethanol and then with two separate portions of acetone. Methanol was added to the dried extracted solids until the solids were completely dissolved to form a fifth solution. Hexane was added to the fifth solution until the solution began to cloud at which time crystals of Δ5-Androstene 3β-ol-7,17-dione began to form at room temperature.

A second crop of Δ5-Androstene 3β-ol-7,17-dione crystals was obtained by cooling the remaining sixth solution.

The resultant product had a melting point of about 235-238° C.

EXAMPLE IV

Immunomodulatory Effect of Δ5-Androstene 3β-ol-7,17-dione (7-Oxo DHEA)

Thirty (30) acclimated and Thoren-unit housed one month old Balb/c mice were separated into six (6) groups of five and bled retro-orbitally under Metofane ® anesthesia to obtain the pre-vaccination serum. Treatments and doses for all groups are set forth in Table 1 below. The DHEA utilized in the trials was obtained from Steraloids, Inc. The 7-Oxo DHEA was synthesized by the procedure of Example III.

TABLE ONE

| Group | Treatment Composition | Steroid Dose/# | Treatment Site |
|---|---|---|---|
| A | 7-Oxo-DHEA | 500 μg/2 | Contralateral |
| B | DHEA | 500 μg/2 | Contralateral |
| C | 7-Oxo-DHEA | 5 μg | Ipsilateral |
| D | Olive Oil | 0 | Ipsilateral |
| E | DHEA | 50 μg | Ipsilateral |
| F | 7-Oxo-DHEA | 50 μg | Ipsilateral |

Mice receiving two treatments (2) received the first treatment three days before vaccination and the second treatment at the time of vaccination. All other treatments were administered at the time of vaccination. The vaccine consisted of 0.17 ml trivalent influenza vaccine (A/Taiwan/H3N2/868, A/Panama/H1N1/91, B/Beijing). Mice were bled three weeks after vaccination to obtain post-vaccination serum.

Determination of the concentration of influenza antibodies in the pre-vaccination and post-vaccination sera were determined by ELISA at dilutions of 1:1000, 1:4000 and 1:16000 with antibody levels reported in optical density at 405 nm with increased optical density indicating increased antibody concentration.

The post vaccination optical density for each group is depicted by dilution in Tables Two (1:1000), Three (1:4000) and Four (1:16000). The baseline optical densities for pre-vaccination sera ranged from values of 0.00 to 0.25 with an average of 0.08. The background optical density averaged 0.1.

TABLE TWO

Optical Density
Post-Vaccination serum
1:1000 Dilution

| Group | Density (Beijing) | Density (Taiwan) | Density (Panama) |
|---|---|---|---|
| A | 2.26 | 1.64 | 1.85 |
| B | 1.25 | 1.59 | 1.76 |
| C | 1.35 | 1.89 | 1.37 |
| D | 0.87 | 1.18 | 1.01 |
| E | 1.71 | 1.44 | 1.17 |
| F | 2.06 | 1.19 | 0.93 |

TABLE THREE

Optical Density
Post-Vaccination serum
1:4000 Dilution

| Group | Beijing | Taiwan | Panama |
|---|---|---|---|
| A | 1.92 | 0.82 | 1.20 |
| B | 0.93 | 0.90 | 1.16 |
| C | 0.85 | 1.43 | 0.64 |
| D | 0.47 | 0.84 | 0.39 |
| E | 1.73 | 0.71 | 0.63 |
| F | 2.25 | 0.61 | 0.35 |

TABLE FOUR

Optical Density
Post-Vaccination serum
1:16000 Dilution

| Group | Beijing | Taiwan | Panama |
|---|---|---|---|
| A | 0.95 | 0.32 | 0.48 |
| B | 0.52 | 0.41 | 0.38 |
| C | 0.38 | 0.35 | 0.27 |
| D | 0.15 | 0.22 | 0.14 |
| E | 0.71 | 0.28 | 0.24 |
| F | 0.99 | 0.23 | 0.09 |

A Bonferroni/Dunn analysis was conducted upon the test results to compare post vaccination antibody responses to combined antigens. The results of this analysis are set forth in Table Two BD (1:1000), three BD (1:4000) and Four BD (1:16000).

TABLE TWO BD

Bonferroni/Dunn Analysis
1:1000 Dilution

| Group | Mean Diff. | Crit. Diff. | P-Value |
|---|---|---|---|
| A B | .483 | .953 | .1262 |
| A C | .267 | .953 | .3946 |
| A D | .707 | 1.004 | .0355 |
| A E | .238 | 1.004 | .4709 |
| A F | .180 | 1.004 | .5857 |
| B C | −.216 | .898 | .4650 |
| B D | .223 | .953 | .4760 |
| B E | −.245 | .953 | .4351 |
| B F | −.303 | .953 | .3344 |
| C D | .439 | .953 | .1635 |
| C E | −.029 | .953 | .9266 |
| C F | −.087 | .953 | .7806 |
| D E | −.468 | 1.004 | .1591 |
| D F | −.527 | 1.004 | .1141 |
| E F | −.058 | 1.004 | .8596 |

TABLE THREE BD

Bonferroni/Dunn Analysis
1:4000 Dilution

| Group | Mean Diff. | Crit. Diff. | P-Value |
|---|---|---|---|
| A B | .493 | .989 | .1326 |
| A C | .219 | .989 | .5004 |
| A D | .597 | 1.043 | .0853 |
| A E | .092 | 1.043 | .7871 |
| A F | −.077 | 1.043 | .8229 |
| B C | −.274 | .933 | .3726 |
| B D | .103 | .989 | .7505 |
| B E | −.401 | .989 | .2202 |
| B F | −.570 | .989 | .0832 |
| C D | .377 | .989 | .2481 |
| C E | −.127 | .989 | .6964 |
| C F | −.296 | .989 | .3639 |
| D E | −.504 | 1.043 | .1446 |
| D F | −.673 | 1.043 | .0529 |
| E F | −.169 | 1.043 | .6217 |

TABLE FOUR BD

Bonferroni/Dunn Analysis
1:16000 Dilution

| Group | Mean Diff. | Crit. Diff. | P-Value |
|---|---|---|---|
| A B | .132 | .456 | .3810 |
| A C | .178 | .456 | .2384 |
| A D | .322 | .481 | .0452 |
| A E | .063 | .481 | .6886 |
| A F | −.010 | .481 | .9495 |
| B C | .046 | .430 | .7448 |
| B D | .190 | .456 | .2077 |
| B E | −.068 | .456 | .6486 |
| B F | −.142 | .456 | .3461 |
| C D | .144 | .456 | .3383 |
| C E | .114 | .456 | .4465 |
| C F | .188 | .456 | .2133 |
| D E | .258 | .481 | .1057 |
| D F | .332 | .481 | .0391 |
| E F | .073 | .481 | .6427 |

CONCLUSIONS

The DHEA and Δ5-Androstene-3β-ol-7,17-dione (7-Oxo DHEA) did not induce clinically apparent toxicity.

The immune response to Taiwan A/H1N1 varied the least between treatment groups. Healthy mice normally respond well to this virus. Accordingly, it appears that treatment with Δ5-Androstene-3β-ol-7,17-dione does not enhance the immune response when the normal immune response is normally "optimally immunogenic".

Δ5-Androstene-3β-ol-7,17-dione contralateral site injection produced the greatest response to the A/Panama/H1N1/91 and B/Beijing viruses. Healthy mice normally do not respond well to this virus. Accordingly, it appears that treatment with Δ5-Androstene-3β-ol-7,17-dione does enhance the immune response when the normal immune response is less than optimal.

What is claimed is:

1. A method for modulating the immune system of a mammal comprising the step of administering to the mammal an effective amount of a steroid selected from the group consisting of Δ5-Androstene-3β-ol-17-one having a $C_7$ substituent selected from the group consisting of oxo, hydroxy and groups convertible thereto by hydrolysis.

2. The method of claim 1 wherein the step of administering the steroid to a mammal comprises the step of administering the steroid to a human.

3. The treatment method of claim 1, wherein the step of administering the steroid comprises the step of injecting the steroid.

4. The treatment method of claim 1 wherein the step of administering the steroid comprises the step of inducing ingestion of the steroid.

* * * * *